United States Patent
Rogers et al.

(10) Patent No.: US 7,496,454 B2
(45) Date of Patent: Feb. 24, 2009

(54) HIGH MAST INSPECTION SYSTEM, EQUIPMENT AND METHOD

(75) Inventors: Peter F. Rogers, Worthington, OH (US); David S. Ellis, Gahanna, OH (US); Pradip N. Sheth, Charlottesville, VA (US); Dominick T. Montie, Charlottesville, VA (US)

(73) Assignee: University of Virginia Patent Foundation, Charlottesville, VA (US)

( * ) Notice: Subject to any disclaimer, the term of this patent is extended or adjusted under 35 U.S.C. 154(b) by 5 days.

(21) Appl. No.: 11/655,807

(22) Filed: Jan. 19, 2007

(65) Prior Publication Data

US 2007/0186671 A1  Aug. 16, 2007

Related U.S. Application Data

(63) Continuation-in-part of application No. 11/184,448, filed on Jul. 19, 2005.

(60) Provisional application No. 60/589,113, filed on Jul. 19, 2004, provisional application No. 60/772,212, filed on Feb. 10, 2006, provisional application No. 60/760,683, filed on Jan. 20, 2006.

(51) Int. Cl.
  *G01L 1/24* (2006.01)

(52) U.S. Cl. .............................. 702/35; 702/33; 702/34; 73/800

(58) Field of Classification Search .................. 702/35, 702/33, 34; 73/800, 865.8; 405/202; 362/250
See application file for complete search history.

(56) References Cited

U.S. PATENT DOCUMENTS

| 6,907,799 | B2 * | 6/2005 | Jacobsen et al. | ........... 73/865.8 |
| 6,980,688 | B2 * | 12/2005 | Wilk | .......................... 382/152 |

* cited by examiner

*Primary Examiner*—Michael P. Nghiem
*Assistant Examiner*—Hien X Vo
(74) *Attorney, Agent, or Firm*—Robert J. Decker

(57) ABSTRACT

An inspection system for removably mounting to a platform movable in relation to a generally upright mast for inspection of the mast has a mounting support assembly removably fixable to the platform. The mounting support assembly for scanning the mast carries a detector device and collecting mast scanned information. A power supply is carried by one or more of the mounting support assembly or the detector device and is connected to the detector device. A communications device is carried by one or more of the mounting support assembly or the detector device and is connected to the detector device for receiving and relaying the collected mast scanned information.

37 Claims, 15 Drawing Sheets

HIGH MAST INSPECTION SYSTEM, EQUIPMENT AND METHOD

CROSS-REFERENCES TO RELATED APPLICATIONS

This application is a continuation-in-part of prior application Ser. No. 11/184,448, filed Jul. 19, 2005, entitled, "Inspection System of Structures and Equipment and Related Method Thereof," which claims benefit of priority from U.S. Provisional Application Ser. No. 60/589,113, filed Jul. 19, 2004, entitled "Integrated Inspection and Light Services System and Method for High Mast Light Poles," Additionally, this application claims benefit of priority from U.S. Provisional Applications Ser. Nos. 60/760,683 and 60/772,212, filed Jan. 20, 2006 and Feb. 10, 2006, respectively, and both entitled "High Mast Inspection System and Method." The entire disclosures of each of the aforementioned patent applications are expressly incorporated herein by reference.

The present application is related to International Application No. PCT/US2005/025544, filed Jul. 19, 2005, "Inspection System of Structures and Equipment and Related Method Thereof," the entire disclosure of which is expressly incorporated herein by reference.

BACKGROUND OF THE INVENTION

The present invention generally relates to inspection of high mast structures typified by high mast lighting towers and more particularly to a unique inspection system and method.

High mast towers are tall, reaching heights of several hundred feet, thus creating a problem of manually inspecting the upper portions of the tower for structural integrity including, inter alia, weld cracks, corrosion, straightness, loss of protective surface finish, dents, punctures, and other structural damage or weakness. Practitioners required to inspect a tower are either required to view the tower from a ground location using unaided eyesight, binoculars or a telescope, a method that does not allow a significantly close inspection of the tower for flaws, or they are required to be raised in a bucket to a higher level to perform a similar analysis, which can be very dangerous and such buckets rarely can reach the upper regions of the high mast towers. These methods of inspection more often are expensive, dangerous, and ineffective.

Other reported experimental methods of inspection involve robotic devices capable of independently climbing a high mast tower. Such inspection methods, while providing closer and more level views of the structure, are problematic in several respects. Existing inspection robots only enable inspection of one view of the tower. Thus, several trips up and down the structure usually are necessary for a full inspection.

Magnetic elements enable these robots to move up and down the structure. Thus, a problem arises when the high mast structure is constructed out of a non-magnetic material and the robot is not capable of climbing the tower. Magnetic adhesion to the tower also limits the weight capacity of the robots, as they often cannot carry all of the desired equipment up the tower. Such robots, beyond containing an already expensive inspection system, also must provide motion and climbing capabilities; thus, adding a great deal of further expense to the system.

A need arises to provide for inspection of high mast towers and other very tall structures that is effective and provides for a level of inspection of a substantial portion of even the tallest high mast towers and other structures, while at the same time avoid being time intensive, prohibitively expensive, or inherently dangerous to practitioners utilizing it. Since most high mast maintenance people are not well trained in crack analysis and operation of highly sophisticated electronic equipment, a desired system would be very simple to use and require little extended education for the operator. It is to such a system that the present invention is addressed.

BRIEF SUMMARY OF THE INVENTION

For purposes of this application, upright structures typified by high masts or poles, such as support light rings, are inspected for an adverse surface condition, such as a flaw, defect, crack, corrosion, erosion, abnormality, irregularity, or other deviation that compromises the integrity and/or functionality of the pole, eventually requiring repair and/or replacement. Such surface conditions often will be referred to as an "anomaly" herein for convenience and not by way of limitation. By "mast" is meant a generally vertical or upright structure, which in the vernacular often is referred to as a pole, tube, rod, shaft, flagstaff, post, wand, tower, or similar upstanding structure. Mast, then, is to be interpreted broadly in accordance with the intent of the disclosure set forth herein.

An inspection system for removably mounting to a platform movable in relation to a generally upright mast for inspection of the mast has a mounting support assembly removably fixable to the platform. A detector device is carried by the mounting support assembly for scanning the mast and collecting mast scanned information. A power supply is carried by one or more of the mounting support assembly or the detector device and is connected to the detector device. A communications device is carried by one or more of the mounting support assembly or the detector device and is connected to the detector device for receiving and relaying the collected mast scanned information.

BRIEF DESCRIPTION OF THE DRAWINGS

For a fuller understanding of the nature and advantages of the present invention, reference should be had to the following detailed description taken in connection with the accompanying drawings, in which.

The drawings will be described in further detail below.

DETAILED DESCRIPTION OF THE INVENTION

The inventive inspection system can be used to check one or more of the following exemplary mast defects: weld cracks, spot loss of galvanization, dents, tears, corrosion (rust), buried foundations, missing/loose nuts, missing/loose access covers, graffiti, and the like. Such inspection system also provides storable and retrievable data files depicting the condition of the mast (including surface condition). The novel inspection system interfaces with a database that includes mast identification (including GPS location). The database created can be used, inter alia, to establish a baseline of a "healthy" mast following initial installation. The database also can be used to create a report establishing the changes/differences between the current inspection and all prior inspections. Moreover, the inventive inspection system is portable and quite usable by current maintenance mast inspection personnel. The novel inspection system, then, is cost effective.

Figure 1:
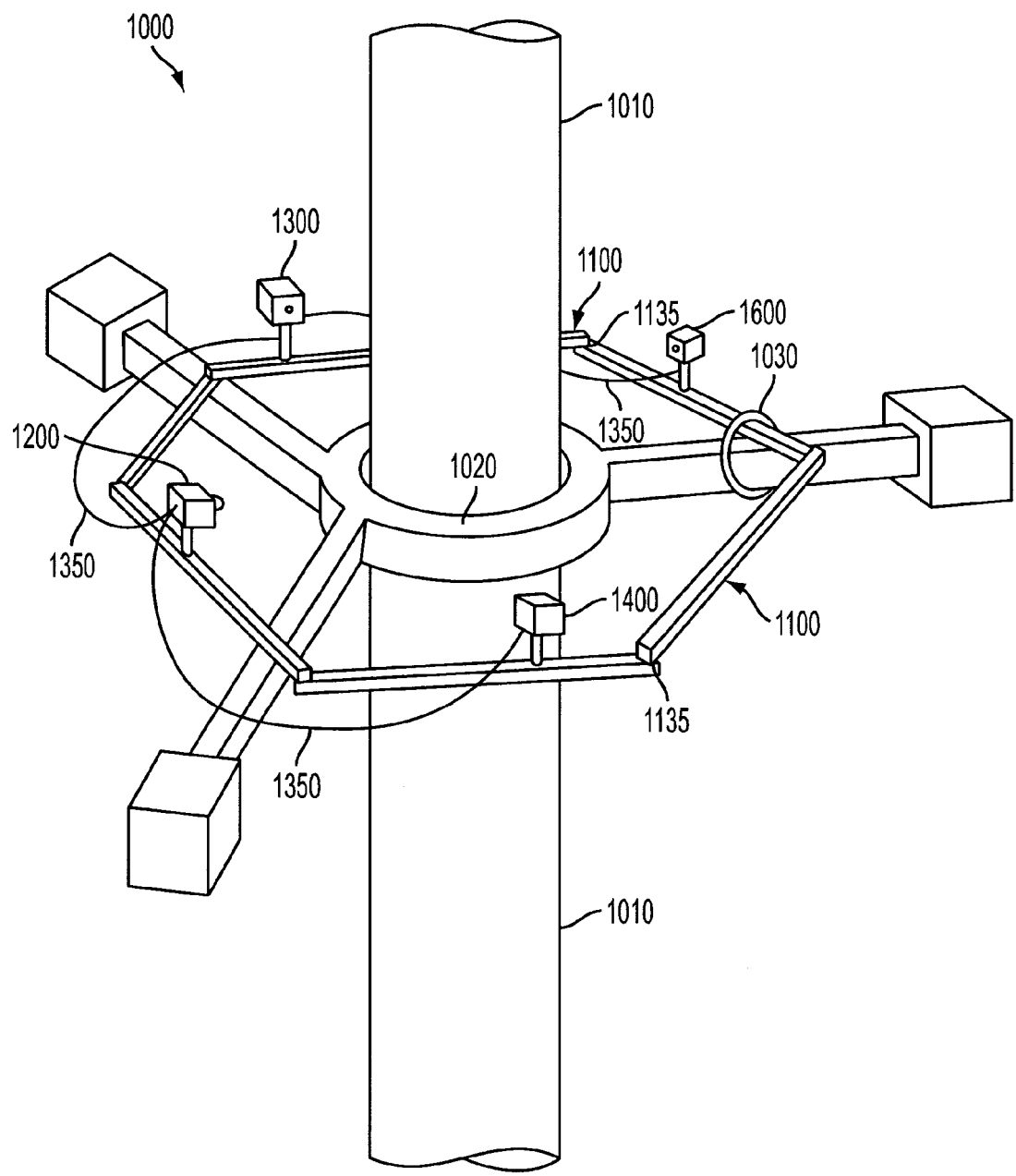
FIG. 1 is a schematic perspective view of an exemplary embodiment of an aspect of the inspection system.
Figure 9:
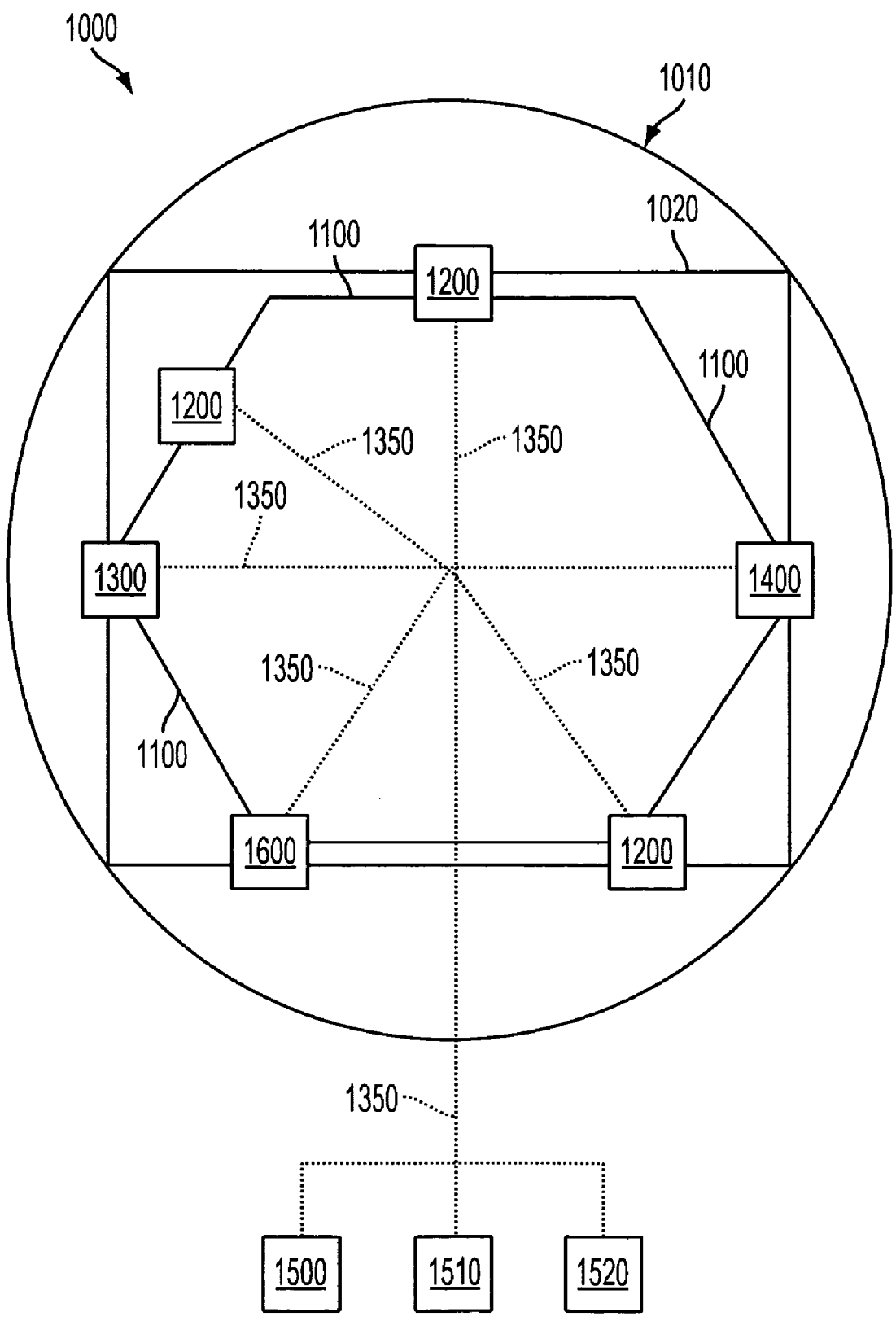
FIG. 9 is a schematic plan view of an exemplary embodiment of an aspect of the inspection system.

FIG. 1 provides a schematic perspective view of an embodiment of an inspection system, 1000, that can be used for inspecting, viewing and/or scanning, a structure, 1010, such a mast pole or the like. A mounting support assembly, 1100, can at least partially enclose, encircle and/or surround structure 1010. Moreover, mounting support assembly 1100 may be located at least partially inside of or on an interior position of a structure, as schematically illustrated in FIG. 9. Further, mounting support assembly 1100 may be located at any variety of locations with respect to the structure, such as, but not limited thereto, above or below. Structure 1010 can be a high mast lighting tower (e.g., roadway, shipping ports, parking lot, and athletic stadiums/facilities), cell tower, and/or an antenna tower, cranes, various vertical piping, vertical tubing, vertical girders, vertical bits, elevator shaft infrastructure, vertical off-shore platform structure, theme park or ball park vertical structure, or any other desired vertical structures or towers. Such vertical structures are generally vertically aligned which includes an angle or alignment. Additionally, the structure may be for example, elevator cables or electrical cables that require inspection. Moreover, it should be appreciated that the structure may be any erected structure requiring inspection, survey or communication therewith. The structure or equipment for inspection may be any vertically-oriented above-surface or vertically-oriented sub-surface structure or equipment. In an embodiment, mounting support assembly 1100 may be any variety of type of bands or rings. Moreover, mounting support assembly 1100 may have any variety of shapes, sizes, dimensions, or attributes so as to accommodate a given platform, 1020, and/or structure 1010 requiring inspection or monitoring. The band or ring may be a wide variety of circumferential shapes or semi-circumferential shapes such as, but not limited to, polygon, hexagon, rectangle, and/or an octagon, etc. Similarly, the band may be a circle, oval, bow, curve, and/or an arc, etc. Mounting support assembly 1100 may be individual components intermittently (i.e., non-continuous) mounted on platform 1020, such as a lowering ring. Platform 1020 can be a lighting rack, maintenance rack, robot, cleaning/monitoring device, an observation deck, top or bottom of elevator (or other specified location), or any structure or equipment that may be found on or with an erected structure or equipment (above or below a surface).

Components of inspection system 1000 can be at least partially supported by or disposed on structure 1010, mounting support assembly 1100 and/or platform 1020, as well as any proximal or remote location from the structure under inspection or monitoring. Components of inspecting system 1000 can be removably mounted on platform 1020, structure 1010, or mounting support assembly 1100, as well as any proximal or remote location from the structure under inspection or monitoring. Mounting support assembly 1100 can be coupled to platform 1020 by a variety of attachment devices or means 1030, for example a tether. Attachment or coupling device 1030 may be a tie rope, cord, hinge, lock, pivot, coupling, key, latch, lug, nail, dowel, nut and bolt, screw, latch, lock, joint and/or a clamp, etc. It should be appreciated that various components of the inspection system or a portion thereof can be permanently or removably affixed to the platform and/or structure.

Inspecting system 1000 further comprises a detector device 1200. Detector device 1200 can comprise a video camera, a digital video camera, thermal imaging camera, radio frequency detector, a still-life camera, ultrasonic device, eddy current device, magnetic particle inspection (MPI), magnetic resonance imaging (MRI) device, any data acquisition device, etc., including for detecting/sensing roll, pitch, yaw, height, direction (compass), and the like. The detector device (as well as the auxiliary device or external device) can itself comprise a robotic system for additional reach on structure 1010. Detector device 1200 is adapted to transmit and/or receive data. Such transmission may be wireless or hard-wired, such as but not limited thereto being implemented using wire, cable, fiber optics, phone line, cellular phone link, RF link, Blue Tooth, infrared link, integrated circuits, and other communications channels. Detector device or means 1200 may have pan, tilt, focus, and/or zoom capabilities. Detector device 1200 may have recording and memory storage capabilities, as well as data processing capabilities. Detector device 1200 may be mounted on mounting support assembly 1100 and/or on platform 1020. It should be appreciated that the detector devices may be used for monitoring, inspecting and/or positioning. Similarly, other devices or instruments may be substituted or added to accomplish the same function(s).

Figure 7:
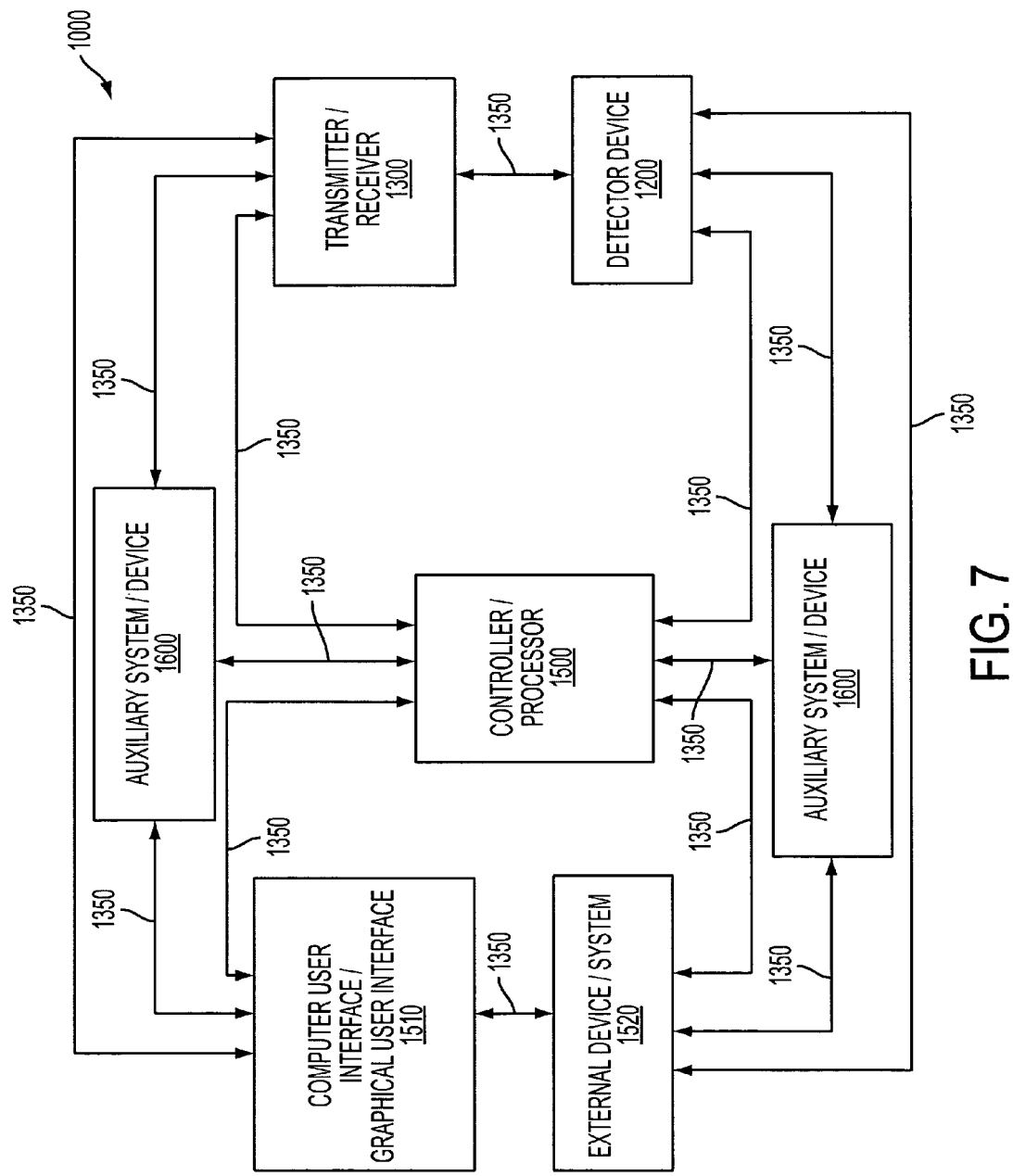
FIG. 7 is a schematic block diagram of an exemplary embodiment of the communication aspect of the inspection system.

Inspection system 1000 further comprises a transmitter and/or receiver 1300. Transmitter/receiver (or transceiver) 1300 may be operatively coupled to detector device 1200. It should be appreciated that the transmitter device, receiver device and detector can be separate or integral units. Moreover, there may be a plurality of transmitter and receiver devices utilized in inspection system 1000 so as to allow any of the modules/devices/instruments/processors to communicate with one another. Transmitter and/or receiver 1300 can be operatively coupled to a controller (as shown in FIG. 7). Transmitter and/or receiver 1300 may comprise a wireless transmitter/receiver and is adapted to receive and transmit data. Accordingly, transmitter and/or receiver 1300 may be adapted to transmit via a physical connection or wireless connection, such as, but not limited to, cable, wire, optical fiber, phone line, cellular phone link, integrated circuit, RF link, Blue Tooth, infrared link and other communications channels, etc. Transmitter and/or receiver 1300 may be removably and/or permanently affixed to platform 1020, structure 1010 and/or mounting support assembly 1100. It should be appreciated there may be a plurality of transmitters and/or receivers 1300 in communication with any of the various components or modules of inspection system 1000 that are mentioned herein. The transmitters and/or receivers may be integral or separate with one another. Moreover, the transmitter and/or receivers may be integral or separate with any of the various components or modules of inspection system 1000 that are mentioned herein.

Inspecting system 1000 may comprise a power supply 1400 as shown in FIG. 1. Power supply 1400 can be operatively coupled to detector device 1200 and/or transmitter and/or receiver 1300. It should be appreciated that power supply 1400 and detector device 1200 (or any other equipment, tool, instrument, system mentioned herein) may be separate or integral units. Similarly, it should be appreciated that power supply 1400 and transmitter and/or receiver 1300 (or any other equipment, tool, instrument, system mentioned herein) may be separate or integral units. Further, it should be appreciated that power supply 1400, transmitter and/or receiver 1300 and detector device 1200 (or any other equipment, tool, instrument, system mentioned herein) may be integral units. Power supply 1400 can be an independent power supply, such as, but not limited to, a generator, battery and/or solar array, etc. Power supply 1400 may be a dependent power supply. It should be appreciated that the power supply may be located on any component of the inspection system or may be proximally located such as at the base of the structure or remotely from the structure (or area under inspection). The transmission of power to the system may be of any available means.

Further, inspection system 1000 also may comprise or be in communication with an auxiliary system/device/instrument 1600, as well as a plurality of such systems/devices/instruments. Such auxiliary system/device/instrument 1600 may include, but not limited thereto, the following: communication devices/systems, robots, global positioning systems, positioning devices/systems, monitoring device/system or laser device or any other device/system/instrument as desired or required.

Figure 2:
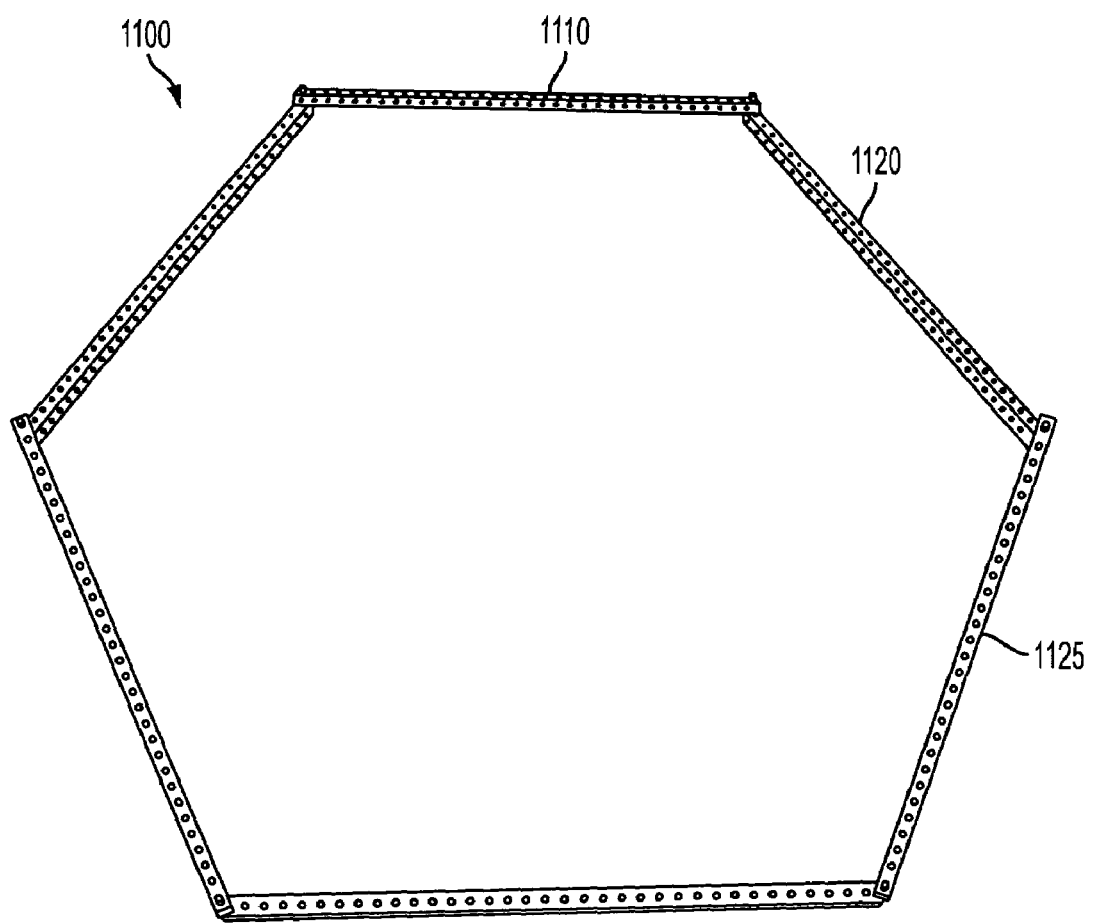
FIG. 2 is a perspective view of an exemplary embodiment of the mounting support assembly.

FIG. 2 is a perspective view of an embodiment of mounting support assembly 1100. Mounting support assembly 1100 may be of a one-piece and/or multi-piece design. Mounting support assembly 1110 may comprise a first segment 1110 and/or a second segment 1120. Second segment 1120 can be releasably coupled to first segment 1110. First segment 1110 and/or second segment 1120 may be detachable from mounting support assembly 1100. Mounting support assembly 1100 may comprise a third segment 1125. It should be appreciated that mounting support assembly 1100 may comprise more than three segments. The mounting support assembly may be formed to provide a complete perimeter around the structure or rather only intermittent or staggered portions around, inside or adjacent to the structure or equipment being inspected or monitored. The segment members may be, but not limited thereto, the following: plates, posts, arms, branches, fingers, frames, legs, rods, sleeves, struts, tracks, trusses, shoulders, or studs, as well as any combination thereof.

Figure 3:
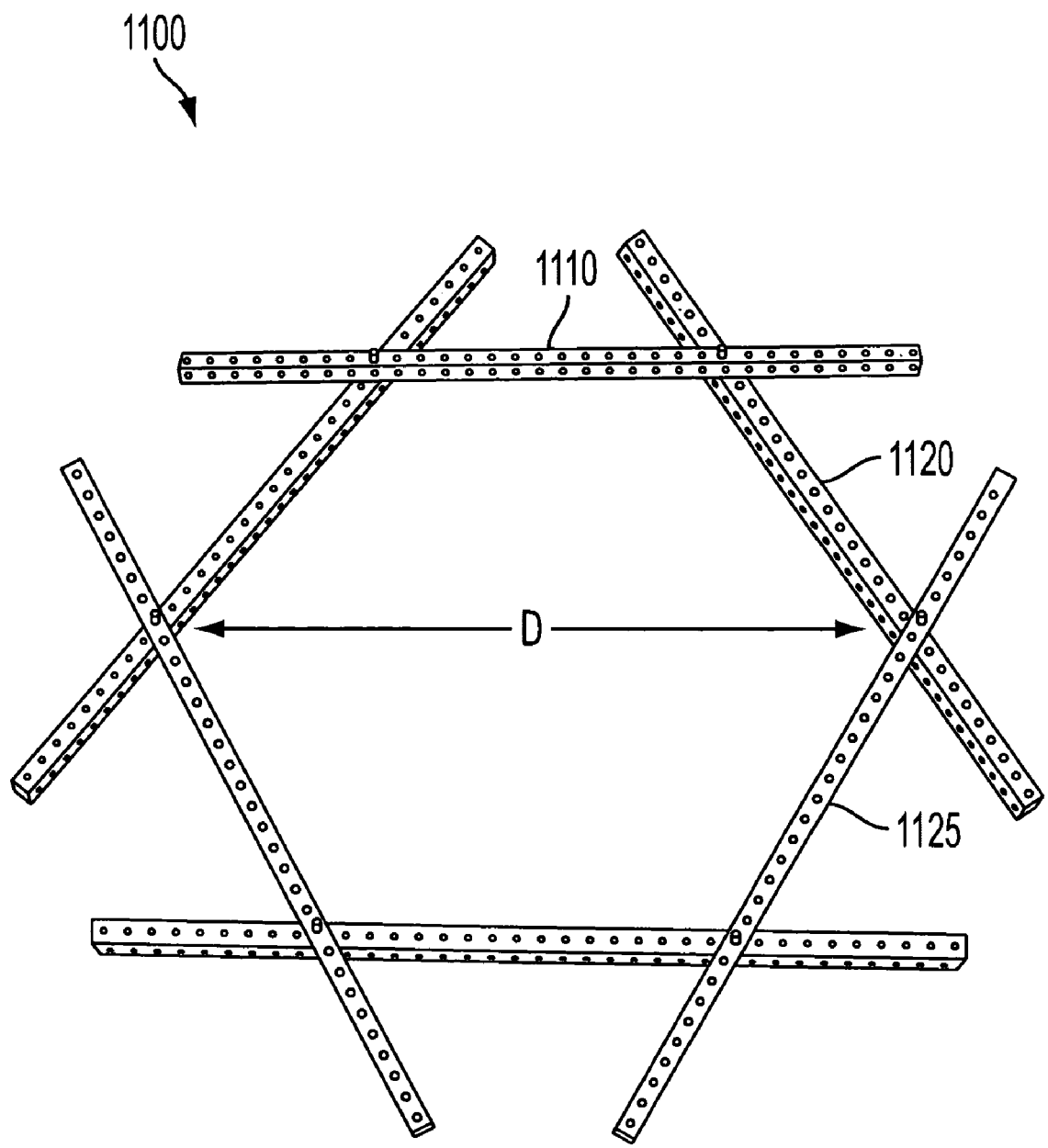
FIG. 3 is a perspective view of an exemplary embodiment of the mounting support assembly.

FIG. 3 is a perspective view of an embodiment of mounting support assembly 1100. Mounting support assembly 1100 may be shaped substantially in the form of a band or ring having a variety of circumferential shapes or semi-circumferential shapes such as, but not limited thereto, polygon, regular polygon, rectangular, hexagon, octagon, circular, oval or arc-shaped, etc. Mounting support assembly 1100 may have an adjustable diameter as referenced as D, for example. The diameter, D, of the band may be any variety of sizes or dimension so as to accommodate, the structure, or equipment, mounting support assembly, platform and/or various components/modules/instruments of the inspection system.. Mounting support assembly 1100 can be constructed of a variety of materials such as, but not limited to metals, steels, alloys, wood, composites, polymers, plastics, or any combination thereof. The material may be any suitable material or composite necessary to accomplish the desired function. The mounting support assembly may be a variety of rigid structures such as perforated steel as shown. By way of example only, poles constructed of non-magnetic materials, a robotic device or given component may use suction cups or similar means to stick to the pole.

Figure 4:
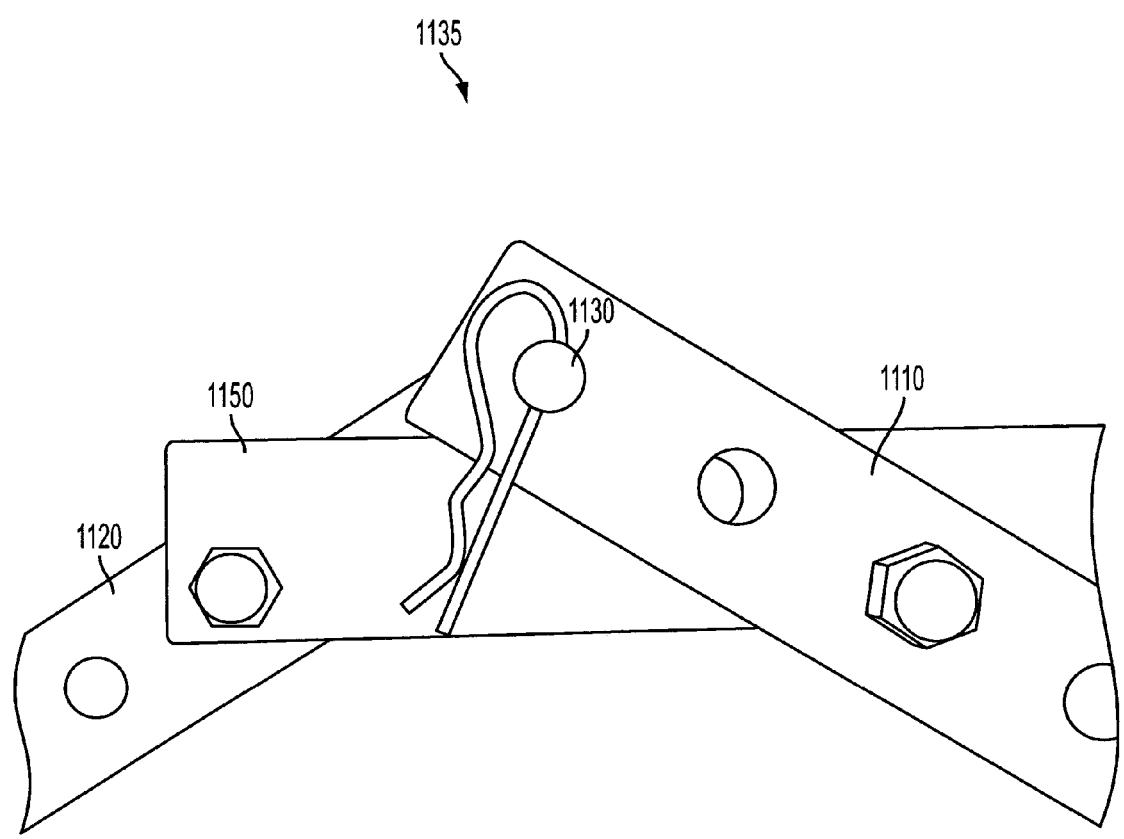
FIG. 4 is a perspective view of an exemplary embodiment of a joint of the mounting support assembly.

Turning to FIG. 4, a perspective view of an embodiment of a joint 1135 of mounting support assembly 1100 is depicted. Joint 1135 may be a variety of coupling means including, but not limited thereto, rope, cord, hinge, pivot, coupling, key, latch, lug, nail, dowel, nut and bolt, screw, latch, lock, joint and/or a clamp, etc. Mounting support assembly 1100 may have removable support plates 1150, such as posts, arms, branches, fingers, frames, legs, rods, sleeves, struts, tracks, trusses, shoulders, or studs. The support plates can fix an angle in mounting support assemblies 1100 to approximately a predetermined degree between segment 1110 and 1120, for example. Segment 1120 can be releasably coupled to another segment 1110 via coupling mechanism 1130 and/or support plate 1150. Coupling mechanism 1130 can be a clamp, rope, lock, pivot, latch, lug, dowel, nut and bolt, screw, bolt, key, pin, cotter pin, tie, or any suitable attachment or binding means. It should be appreciated that mounting support assembly may be coupled with joints 1135 without the use of support plates 1150.

Figure 5:
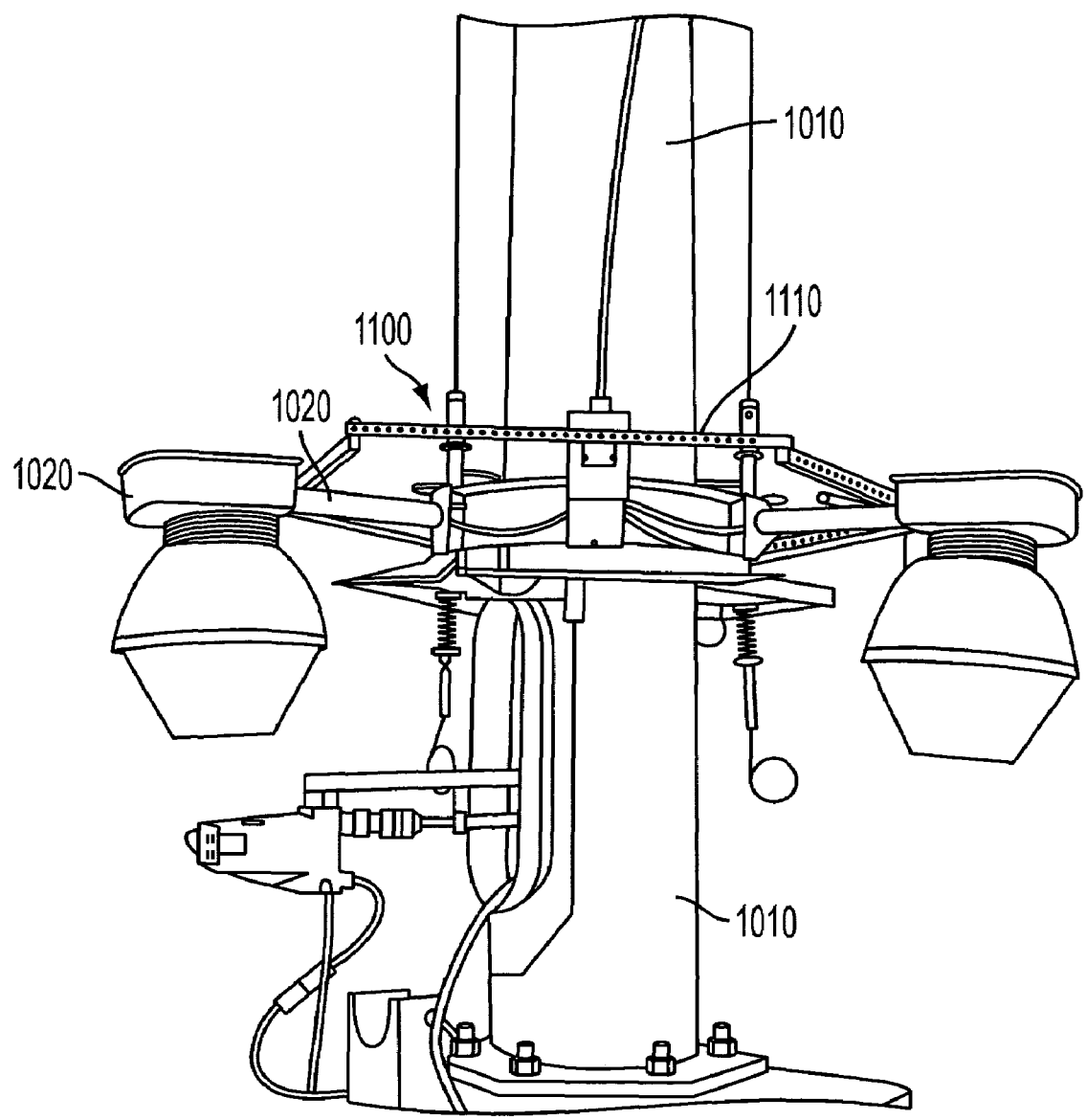
FIG. 5 is an operative view of an exemplary embodiment of the mounting support assembly in relation to the platform near the base of the structure for the inspection system.
Figure 6:
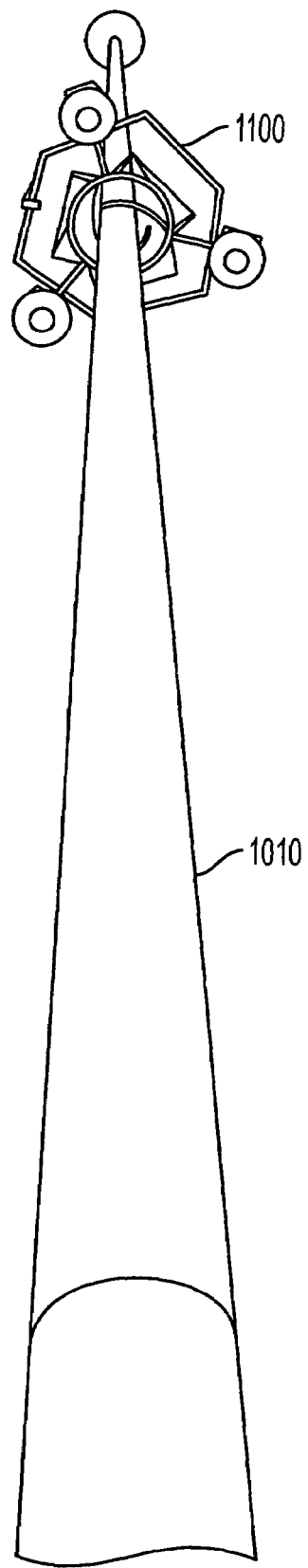
FIG. 6 is an operative view of an exemplary embodiment of the mounting support assembly in relation to the platform near the apex of the structure for the inspection system.

Next, turning to FIG. 5, an operative view of an embodiment of the mounting support assembly in relation to the platform near the base of the structure is illustrated. Platform 1020 can be lowered to a position at and/or near the base of structure 1010. The various components or modules of inspection system 1000 can be disposed on platform 1020 and/or structure 1010 while the platform is in a lowered state. As platform 1020 is raised, and/or at intermittent stopping points on its path of elevation, the inspecting system captures data regarding structure 1010. The inspection system can perform the inspection up to the apex of the platform path or any point between the base and the apex (as shown in FIG. 6). The platform can be lowered and the inspection components can be removed or attended to as desired or required.

Turning to FIG. 7, a schematic block diagram of an embodiment of the communication aspect of inspection system 1000 is illustrated. The data can be captured by the detector device 1200 (or any other equipment, tool, instrument, system, module, mentioned herein), wherein the data can be transferred between the transmitter and/or receiver 1300 from the detector device 1200 (or any other equipment, tool, instrument, system, module mentioned herein). The data can be transmitted by the transmitter and/or receive 1300 to a controller/processor 1500. The controller/processor 1500 may comprise a mobile or stationary computing or processing device, television, oscilloscope and/or various measuring or interactive devices/instruments/equipment, etc. A technician or user can analyze (or process as deemed appropriate) this data as it is received by the controller/processor and/or record the data for future analysis or as desired. The technician or user can use a graphical user interface/computer user interface 1510 (as shown FIG. 8 and FIG. 10) to send/receive control signals or data from the controller/processor device to the transmitter and/or receiver 1300, detector device 1200 (or any other equipment, tool, instrument, system mentioned herein) and/or auxiliary system/device/instrument 1600. Examples of the controller/processor may be a variety of processors implemented using hardware, software or a combination thereof and may be implemented in one or more computer systems or other processing systems, such as general purpose computer or personal digital assistants (PDAs).

It should be appreciated that the communication of data and information transferred among the modules and components of the inspecting system may be implemented using software and data transferred via communications interfaces that are in the form of signals, which may be electronic, electromagnetic, optical, RF, infrared or other signals capable of being received by communications interfaces. The signals may be provided via communications paths or channels 1350 (or any other communication means or channel disclosed herein or commercially available) that carries signals and may be implemented using wire or cable, fiber optics, integrated circuitry, a phone line, a cellular phone link, an RF link, an infrared link and other communications channels/means commercially available.

Other examples of the computer user interface/graphic user interface 1510 may include various devices such as, but not limited thereto, input devices, mouse devices, keyboards, monitors, printers or other computers and processors. The computer/graphic user interface may be local or remote. It should be appreciated that there may be one or more computer user interface/graphic user interface. 1510 that may be in communication with any of the components, modules, instruments, devices, systems and equipment discussed herein. For example, the computer user interface/graphic user interface 1510 may be remotely located. Such a remote communication of the computer user interface/graphic user interface 1510 may be accomplished a number of ways including an uplink/communication path 1350 to a cell telephone network (e.g., external device/system 1520) or satellite (e.g., external device/system 1520) to-exchange data with a central processing point (e.g., external device/system 1520).

The inspection system may also be in communication with an external device(s) or system(s) 1520 such as at least one of the following transmitters, receivers, controllers/processors, computers, satellites, telephone cell network, PDA's, workstations, and other devices/systems/instruments/equipment. Aforementioned external device/systems 1520 may be comprised of one or plurality and may be locally and/or remotely located.

Further, inspection system 1000 may also comprise or be in communication with an auxiliary system/device/instrument 1600, as well as a plurality of such systems/devices/instruments. Such auxiliary system/device/instrument 1600 may include, but not limited thereto, the following: communication device/system, robot, global positioning system (GPS), laser devices, positioning device/system, monitoring device/system, laser device or any other device/system/instrument as desired or required. Aforementioned auxiliary device/system/instrument 1520 may be comprised of one or plurality and may be locally and/or remotely located.

Figure 8:
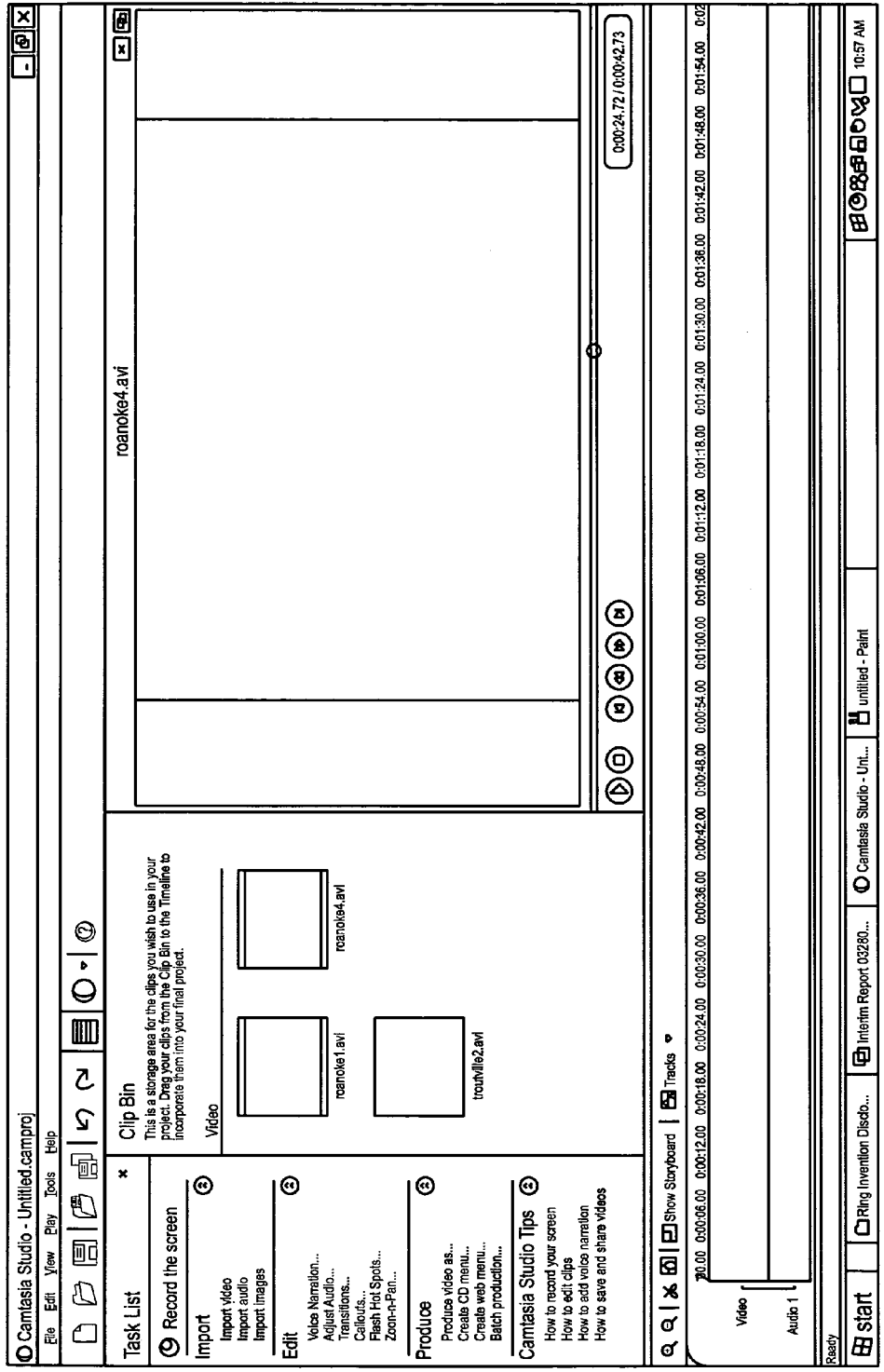
FIG. 8 is an operative view of an exemplary embodiment of the graphical user interface/computer interface of the inspection system.

FIG. 8 shows an embodiment of a computer/graphic user interface 1510. User interface 1510 can comprise a graphical user interface as shown. User interface 1510 can display data received and/or transmitted. The control signals sent from or to user interface 1510 can alter the functionality of the detector, such as, but not limited to, positioning, monitoring, inspecting, panning, tilting, zooming, and/or focusing, etc.

The control signals sent from or to user interface 1510 also can alter the functionality of the any component or module of the inspection system mentioned herein including, for example, the external device, auxiliary device, and controller/processor.

Turning to FIG. 9, a schematic plan view of an embodiment of inspection system 1000 that can be used for inspecting, viewing, positioning and/or scanning, etc. structure 1010 is shown. Mounting support assembly 1100 is located at least partially inside of or on the interior position of structure or equipment 1010, as schematically illustrated in FIG. 9. Structure 1010 may be a variety of structures or equipment such as, but not limited thereto, towers, piping, tubing, girders, shafts, elevator shafts, etc. Additionally, inspection system 1000 structure may be adjacent or proximal to the structure or equipment being inspected, monitored, analyzed or positioned. Any one or all of the components/modules as illustrated and discussed throughout—detector device 1200, transmitter and/or receiver 1300, power supply 1400, controller/processor 1500, user interface 1510, external device 1520, and auxiliary systems/devices/instruments 1600—may be in communication via communication path/channel 1350. It should be appreciated that anyone of the aforementioned components/modules may be singular or plural as well as separate or integral with other respective components/modules.

Figure 10A:
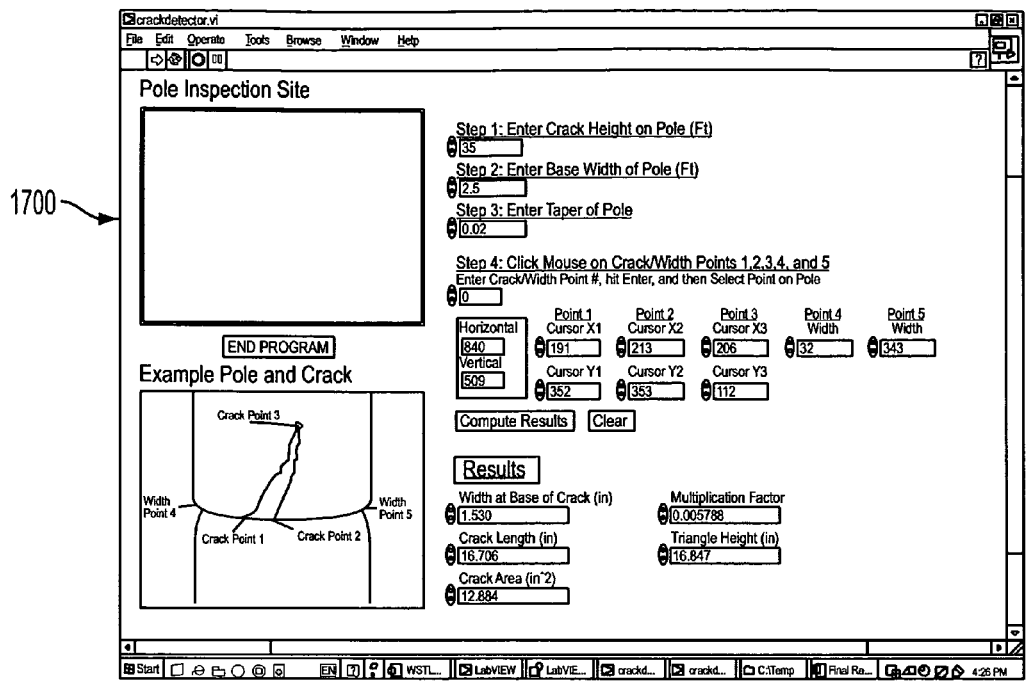
FIG. 10(A) is an operative view of an exemplary embodiment of the graphical user interface/computer interface of the inspection system.
Figure 10B:
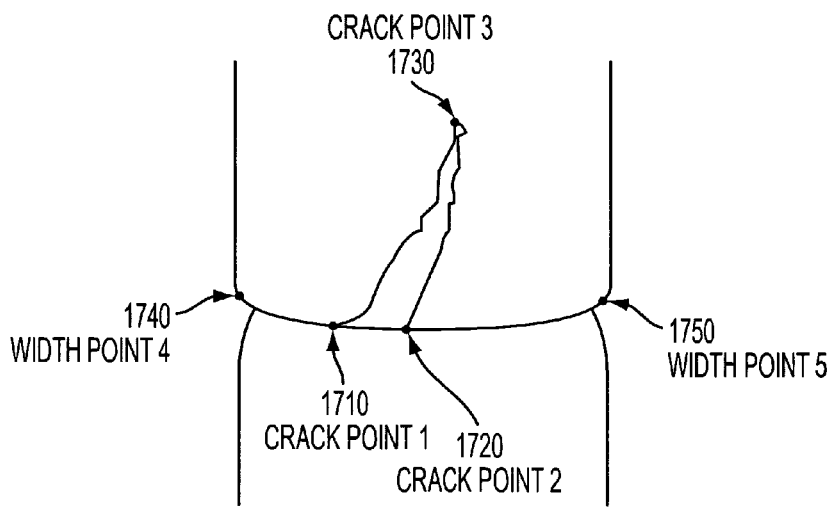
FIG. 10(B) is an enlarged partial view of the interface shown in FIG. 10(A)

FIG. 10(A) shows an embodiment of a computer/graphic user interface 1700. User interface 1710 can comprise a graphical user interface as shown. User interface 1700 can display data received and/or transmitted. FIG. 10(B) is an exploded partial view of the interface shown in FIG. 10(A).

Computer processor(s) 1500, as discussed throughout, may be comprised of hardware, software or any combination thereof to process the data to determine the outcome or interesting result of an inspection on a high mast pole or given structure or equipment. It should be appreciated that controller/processor 1500 may be adapted with a variety of software and/or hardware having a number of anomaly detection (surface and/or subsurface) algorithms or process capabilities. In an embodiment, the processor may include the following algorithm for purpose of inspecting a crack or flaw on a structure (e.g., pole): receive the actual width of the base of the structure (e.g., pole); receive the distance between the base of the structure (e.g., pole) to the crack or flaw, receive the actual width of the structure (e.g., pole) at the crack or flaw; receive the crack points or flaw points (as referenced as 1710, 1720, and 1730) and width points (as referenced as 1740 and 1750) data according to the locations illustrated in FIG. 10(B) so as to provide "screen image data"; and calculate the actual dimensions of the crack or flaw based on the relationship between the "screen image data" pole width with the actual pole with at the crack or flaw. A benefit of this method is that all crack or flaw measurements can be performed either in the field or at remote location (e.g., home office or satellite location) after the field data have been collected.

In an embodiment, the following method may be implemented:

1. Utilize a measuring device, such as tape, laser, or any type of distance determining device to measure the actual width of the base of the pole;
2. Utilize an ultrasonic distance measurement device or manual measurement (or other automated device) to measure the distance from the base of the pole to the crack or flaw;

3. Calculate (e.g., via software) the actual width of the pole at the crack or flaw, which may be accomplished from knowledge of the pole taper or other information;
4. Calculate (e.g., via software) the screen image dimensions of the crack or flaw, as shown in FIG. 10(B) as references 1700, 1720 and 1730 (for example), and entered accordingly, as compared to the screen image width of the pole, as shown in FIG. 10(B) as references 1740 and 1750 (for example), and entered accordingly; and
5. Calculate (e.g., via software) the actual dimensions of the crack or flaw based on the relationship between screen image pole width (e.g., FIG. 10(B))and actual pole width at the crack or flaw.
6. Using only two measured pieces of data, and the manufacturer supplied pole taper specifications, the software (e.g., prototype LABVIEW®-based software program or other available programming languages) produces-crack or flaw dimensions (height and width).

A benefit of this method, but not limited thereto, is that all crack measurements can be performed either in the field or at the home office after field data have been collected.

In this application, the terms "computer program medium" and "computer usable medium" are used to generally refer to media such as removable storage drive, a hard disk installed in hard disk drive, and signals. These computer program products are means for providing software to computer system. The various embodiments include such computer program products. Computer programs (also called computer control logic) are stored in main memory and/or secondary memory. Computer programs may also be received via communications interface and/or communication path/channel. Such computer programs, when executed, enable computer system to perform the features of the present invention as discussed herein. In particular, the computer programs, when executed, enable processor to perform the functions of various embodiments of the present invention. Accordingly, such computer programs may represent controllers of a computer system. In an embodiment where the invention is implemented using software, the software may be stored in a computer program product and loaded into computer system using removable storage drive, hard drive or communications interface. The control logic (software), when executed by the processor, causes the processor to perform the functions of the invention as described herein. In another embodiment, the invention is implemented primarily in hardware using, for example, hardware components such as application specific integrated circuits (ASICs). Implementation of the hardware state machine to perform the functions described herein will be apparent to persons skilled in the relevant art(s). In yet another embodiment, the invention is implemented using a combination of both hardware and software. The methods described above could be implemented in a variety of available program languages.

The following disclosure is of a commercially available embodiment of the disclosed high mast inspection system.

Camera Pod Assembly

Figure 11:
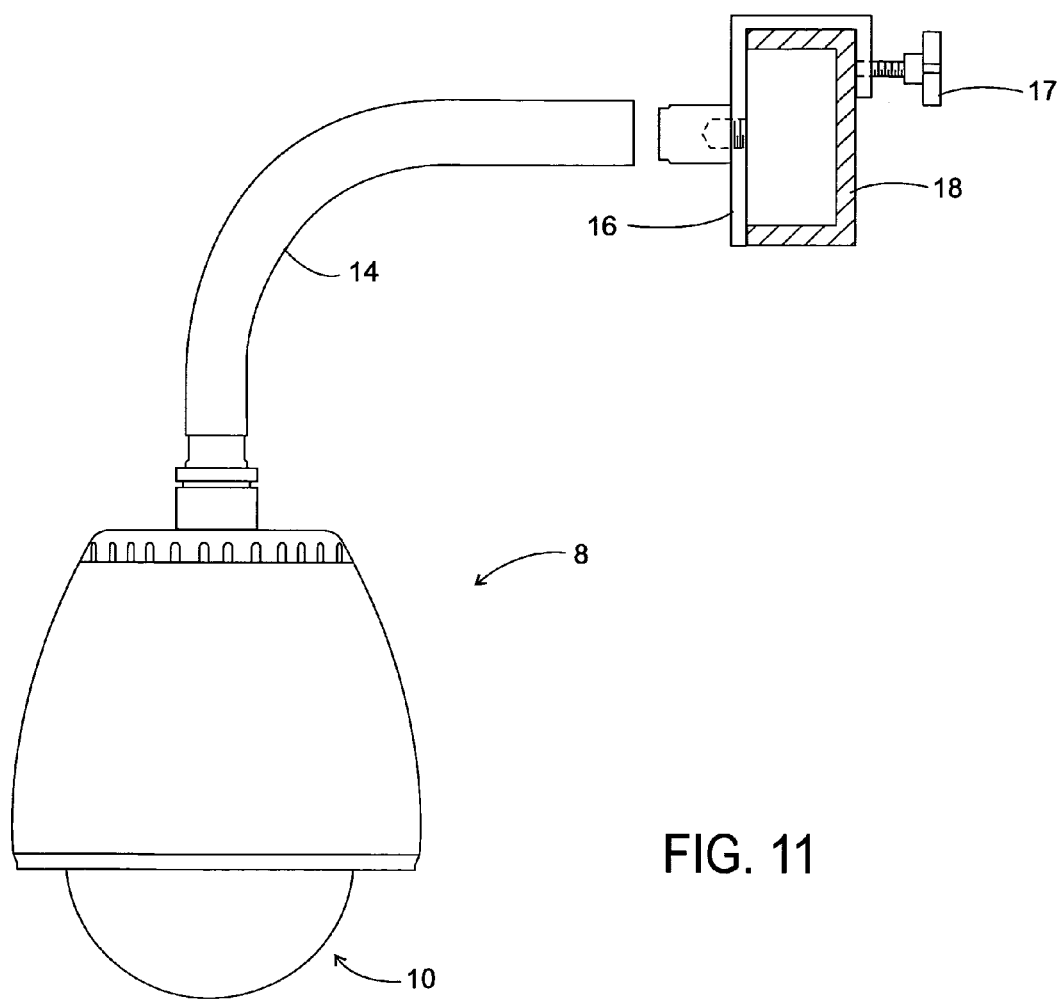
FIG. 11 is a plan view of a commercial camera pod assembly (detector device) affixed to a luminaire ring.

Referring now to FIG. 11, a camera pod assembly, 8, includes a power supply, camera pod, mounting bracket assembly, and wireless communication transceiver. The camera pod assembly is adapted to be affixed to luminaire ring 1020 of a high mast light tower with the mounting bracket assembly. Referring to FIG. 11, essentially, camera pod assembly 8 includes a camera pod, 10, which includes a still/video camera remotely controlled (pan, tilt, zoom, and focus) and which is powered by a power source, 12 not seen in FIG. 11), which suitably is a rechargeable battery. Camera pod 10 is removably affixed to a bracket assembly, 14, which can be quickly connected/disconnected to luminaire ring 1020 with a bracket, 16, which conveniently operates with a "thumb screw", 17, hand operable to quickly connect and disconnect camera pod assembly 8 to luminaire ring 1020 or any other component of a light ring assembly. A variety of other quick connect/disconnect designs can be envisioned and it matters only that a service technician can readily operate the connect/disconnect assembly quickly and that it reliably stay connected. Finally, camera pod assembly 8 carries a wireless communications transceiver and antenna (not seen in the drawings but self-contained within camera pod 10) for transmitting the camera-captured images (or other detector outputs) to a near or remote receiver/transceiver and for receiving signals for operating (e.g., pan, tilt, zoom, and focusing) the camera. The particular camera pod illustrated has such wireless communications transmitter built into it; although, a separate such unit can be provided. A direct-wired configuration could be used for this and for other related applications.

While a battery associated with each camera pod currently is contemplated, the operator can connect a single battery or power source carried, for example, by one of the camera pods to the other camera pods for power. Alternatively, other power sources, such as, for example, solar collectors, fuel cells, or the like, may find utility for powering the camera pods and such other power sources are within the scope of the present invention.

Typically, between 3 and 4 camera pod assemblies are used for any given mast being inspected to ensure a complete 360-degree view of the structure. The number of cameras is an input variable to the recorder software (see below). As illustrated in FIG. 11, an Internet Protocol (IP) based camera is provided with its own power source and an IEEE 802.11 wireless transceiver. Camera control and images are sent digitally through the wireless network. Low-level wireless protocols are auto-configuring. Wireless PC card transceivers with small ¼wave diverse antennas are used in the camera pods.

Most high mast lamping systems lend themselves to either three or four camera pod assemblies, depending upon the number of luminaires (lamps). Regardless, it is desirable to view all 360° circumference of the pole so that the entire exterior surface can be inspected and recorded. In a 3-camera system, each camera has the potential to view its own 120° sector of the, pole with some overlap with the adjacent cameras. In a 4-camera system, each camera has the potential to view its own 90° sector of the pole with significant overlap, which is slightly better in that a flatter image is viewed with less distortion. Cameras also may be zoomed in so as to have as little image overlap as possible and to yield images with better definition of the pole surface.

High Mast Viewer/Transceiver

Figure 12:
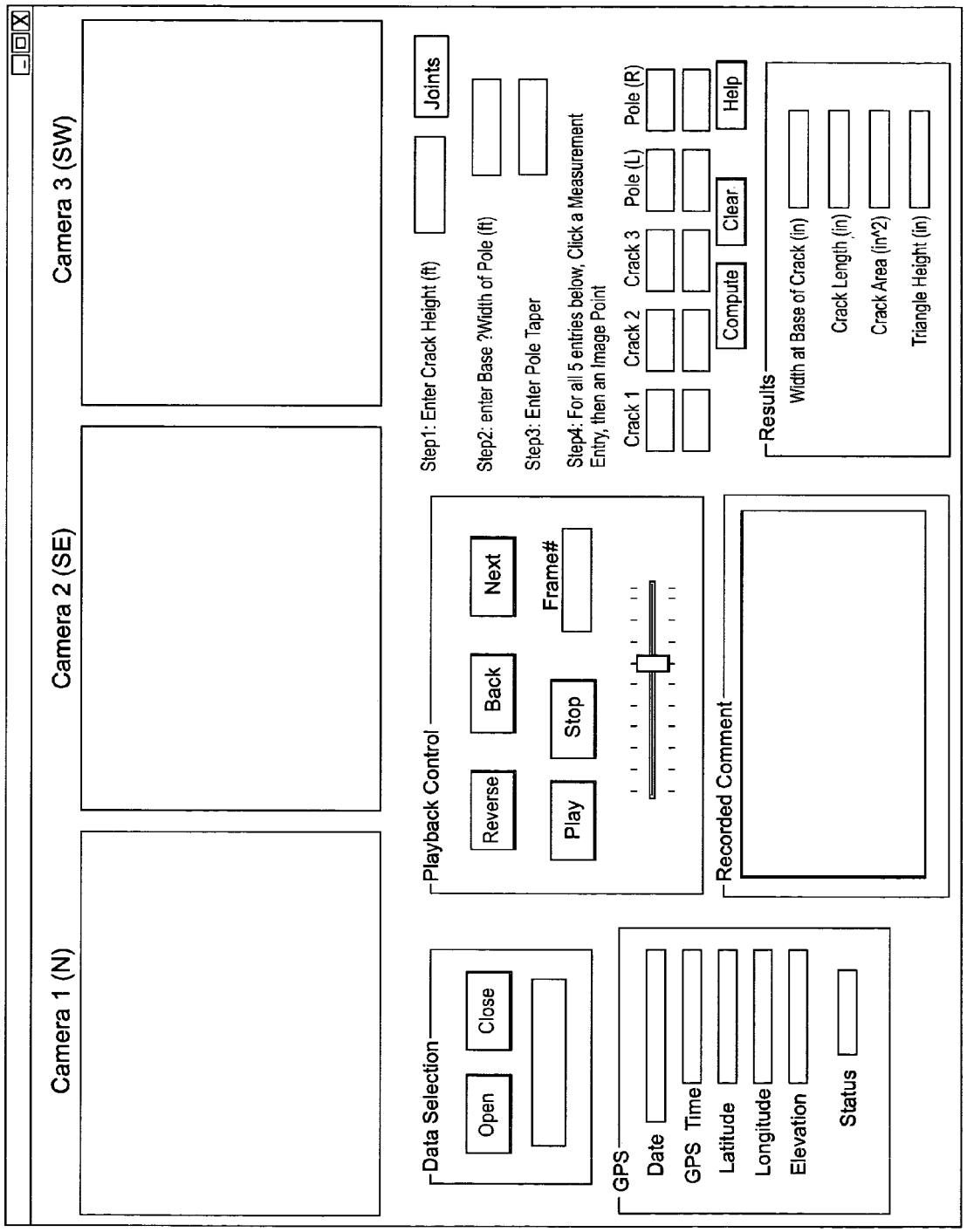
FIG. 12 is an image of a commercial viewer/transceiver screen showing screens where images of a mast crack and different sides of a mast are displayed.

FIG. 12 shows the MastCheck™ viewer screen. Images recorded using the MastCheck™ recorder (See FIG. 14) are presented. From one to four images may be shown. The images may be played back, stopped, and manually viewed frame by frame. Frame numbers are recorded with the image and are displayed for reference purposes. Images may be enlarged, edited, entitled, and/or saved as individual or sets of images.

Global Positioning System (GPS) information, showing the pole location, taken at the time of recording is shown in the lower left. The recording operator's comments are included in the bottom center and the crack analysis section on the lower right.

The host recorder workstation (laptop computer) uses a battery powered wireless access point (AP) for all communications with the cameras. These form a network that uses a fixed architecture with IP addresses. Low-level wireless protocols are auto-configuring. The workstation AP also has a high gain panel type diversity antenna to insure a quality signal, and high data throughput. This is placed near the base of the pole or on the maintenance vehicle aimed upward at the cameras.

Crack Analysis Help Screen

The current commercial version utilizes the crack analysis regimen, as described above in connection with FIGS. 10A and 10B, and the description thereof.

High Mast Recorder/Transceiver

Figure 13:
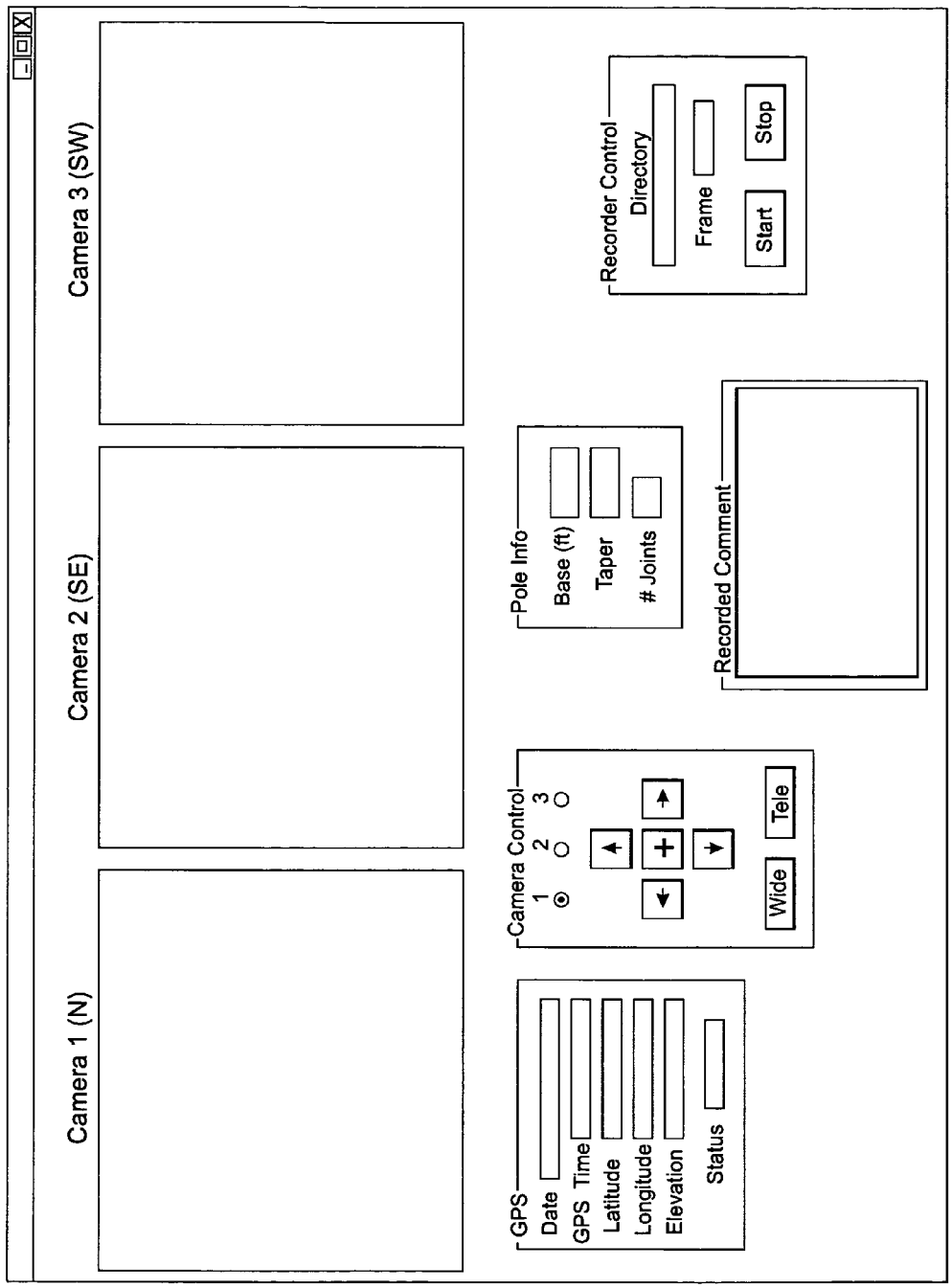
FIG. 13 is an image of the commercial viewer/recorder screen.

FIG. 13 shows the MastCheck™ recorder screen. Images are recorded from one up to four wireless camera pods (across the top). All of the images are recorded independently or at the same time. The recorder also may be paused during the recording. Frame numbers are recorded with the image and are displayed for reference purposes.

Global Positioning System (GPS) information, showing the pole location, is recorded at the start of recording and is shown in the lower left. Pole information is entered and recorded for use in later analysis. The recording operator may also make general comments about the recording. Record control is in the lower right of the screen. A standard MS WINDOWS or similar directory holds all of the recorded data. Comments and pole info are saved at the end of the recording.

Communication Block Diagram for the Inspection System

Figure 14:
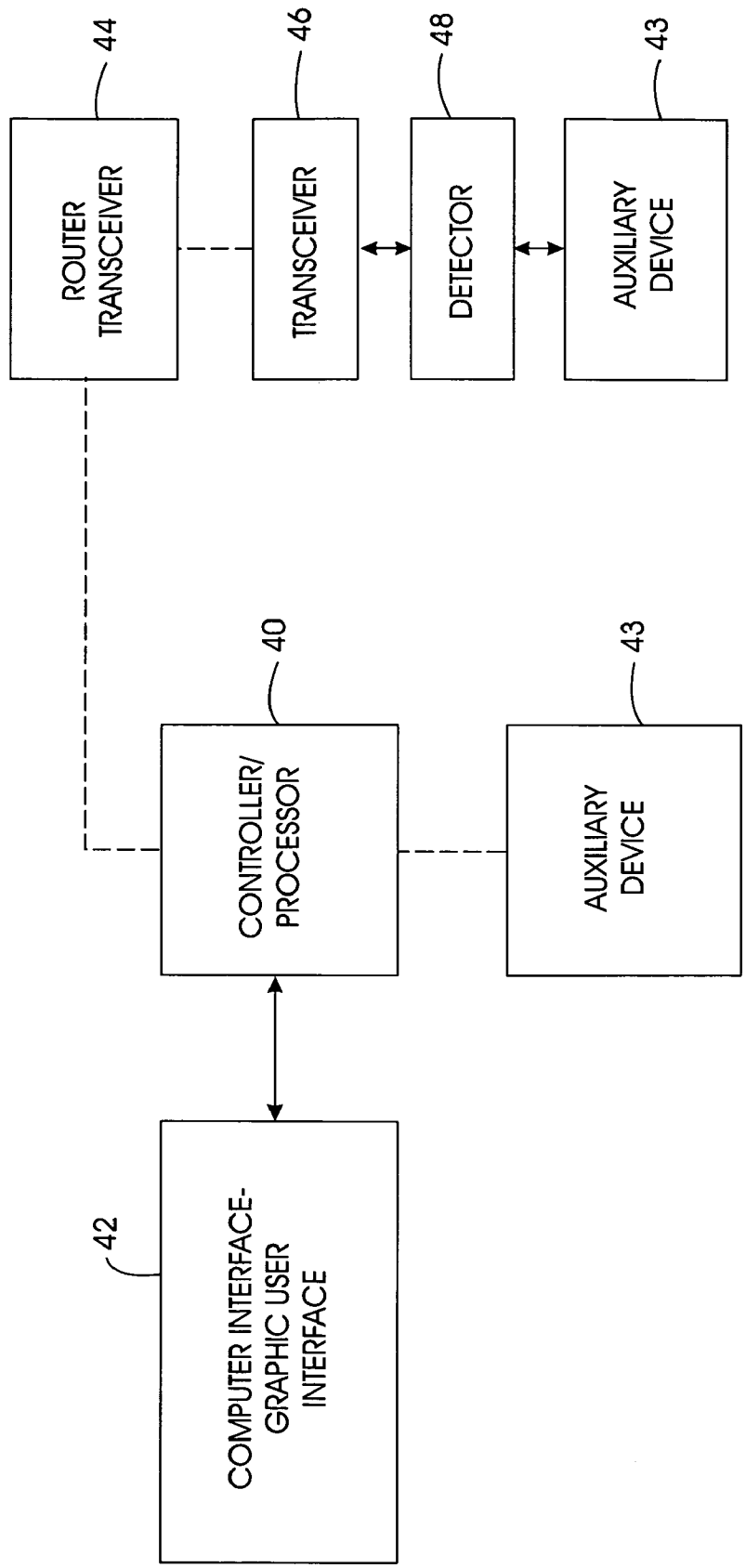
FIG. 14 is a schematic block diagram of a commercial embodiment of the communication aspect of the inspection system.

The block diagram of FIG. 7 was simplified for a commercial version of the disclosed high mast inspection system, as shown in FIG. 14. A controller/processor, 40, drives a computer interface/graphic user interface or display, 42, enabling the operator to visualize the data generated by the detector device. Controller/process 40 can be located remote from the mast poles being surveyed, though it can be carried along with the operator in the field. Auxiliary device(s) (GPS, for example), 43, can be inputted directly into controller/processor 40, if desired.

A transceiver/router, 44, optionally can be used to transmit data to controller/processor 40 and to receive instructions from controller/processor 40. A transceiver, 46, detector, 48, and auxiliary device(s) 43, often are a single unit, such as camera pod assembly 8; although, separate units can be used. Any or all of the communication between any or all of the devices in FIG. 15 can be via hard wire and/or wireless communication.

Functional Flow Diagram for the Inspection Operation

Figure 15:
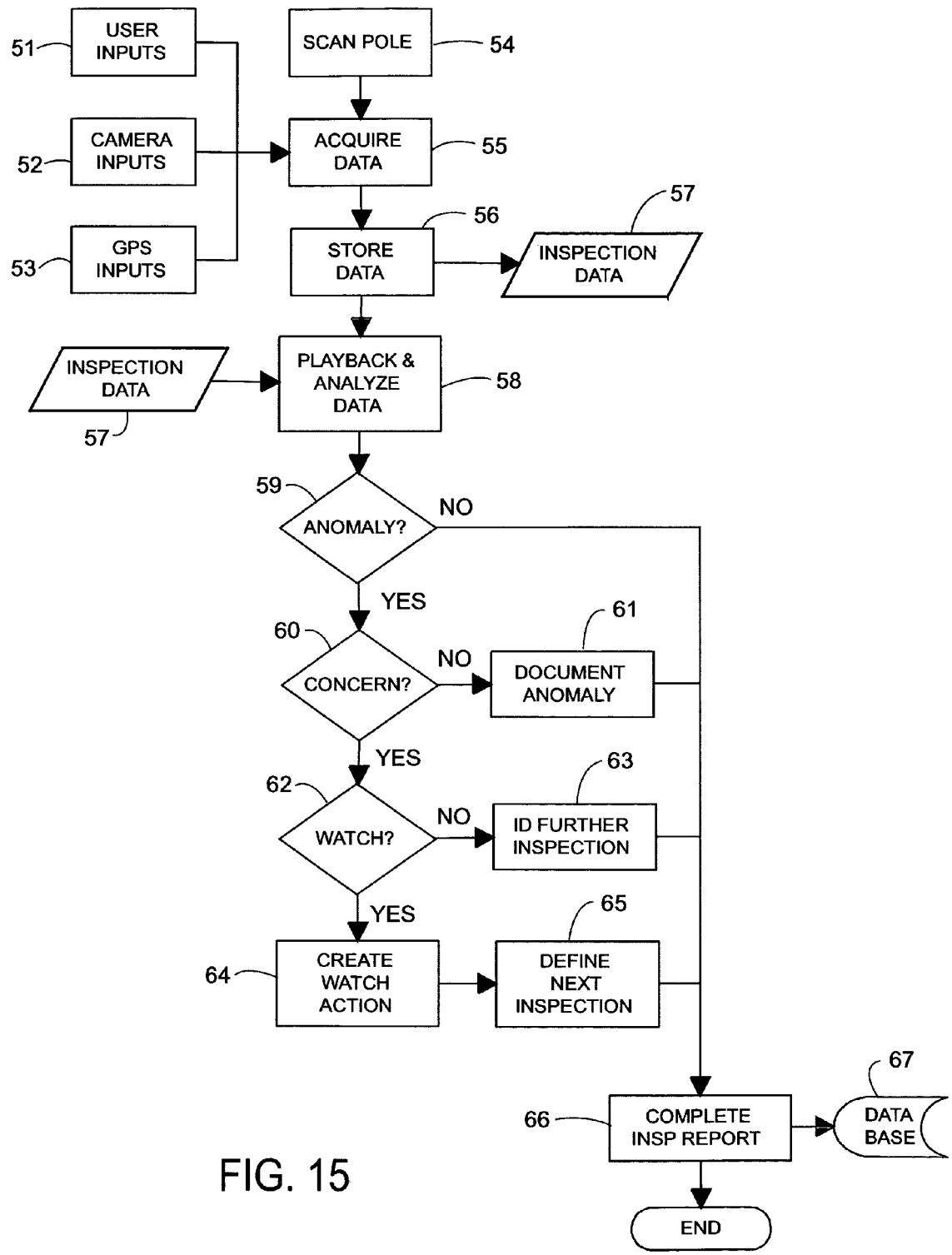
FIG. 15 is a functional flow diagram of a commercial version of the disclosed inspection system.

The functional flow diagram for the operation of the inventive inspection system is set forth in FIG. 15. Functional inputs include, inter alia, user inputs, block 51; camera input, block 52; GPS input, block 53; and the pole scan, block 54. The functional inputs become acquired data, block 55, which are stored, block 56. The stored data in block 56 can be outputted to a computer or similar display/analysis device for becoming inspection data, block 57.

The inspection data in block 57 also can be inputted along with stored data from block 57 for playback and analysis, block 58, to determine whether an anomaly has been detected, decision block 59. If no anomaly is detected, an inspection report is completed, block 66, which is recorded in a database, block 67, and the inspection is completed (ended).

If, however, an anomaly is detected, a determination as to whether the anomaly is of concern is made at decision block 60. If the decision is made that the anomaly is not of concern, the anomaly is recorded, block 61, and the inspection report is made, as described before.

If the anomaly is of concern, a determination as to whether to put the anomaly on watch status, decision block 62, is made. If no immediate watch is required, the anomaly is cataloged for note at a future inspection, block 63, and the inspection report is made, as before. If the watch decision is positive, then an action watch is created, block 64, and a next inspection of the anomaly is made, block 65, and this action/decision is recorded on the inspection report.

The foregoing functional flow diagram establishes a baseline for existing poles and crack data and other characteristics such as, for example, corrosion collected for other poles, an opportunity exists for monitoring the progress of cracks and other characteristics and employing predictive algorithms for pole maintenance and/or replacement. While such analytical tools have not yet been developed, the inventive inspection system now will enable the skilled artisan to develop and apply these and other analytical tools to high mast poles.

While the invention has been described with reference to various embodiments, those skilled in the art will understand that various changes may be made and equivalents may be substituted for elements thereof without departing from the scope and essence of the invention. In addition, many modifications may be made to adapt a particular situation or material to the teachings of the invention without departing from the essential scope thereof. Therefore, it is intended that the invention not be limited to the particular embodiments disclosed, but that the invention will include all embodiments falling within the scope of the appended claims. All citations referred herein are expressly incorporated herein by reference.

We claim:

1. An inspection system for removably mounting to a platform movable in relation to a generally upright mast for inspection of said mast, which comprises:
   (a) a mounting support assembly removably fixable to said platform;
   (b) a detector device carried by said mounting support assembly for scanning said mast and collecting mast scanned information, wherein said detector device is one or more of: thermal imaging detector, radio frequency detector, thermal imaging camera, image acquisition device, charge coupler device (CCD), magnetic particle inspection (MPD), video camera, digital still-camera, magnetic particle inspection (MPI), ultrasonic device, magnetic eddy current device, or magnetic resonance imagining (MRI) device;
   (c) a power supply carried by one or more of said mounting support assembly or said detector device and connected to said detector device; and
   (d) a communications device carried by one or more of said mounting support assembly or said detector device and connected to said detector device for receiving and relaying said collected mast scanned information.

2. The inspection system of claim 1, further comprising:
   (d) a first wireless communication transceiver carried by one or more of said mounting support assembly or said detector device and connected to said detector device and connected to said detector device to receive data from said detector device; and (e) a remotely located, second wireless communications transceiver/router in communication with said first wireless communication transceiver for receiving data from said detector device.

3. The inspection system of claim 1, further comprising:

(f) a processor connected to said wireless communications transceiver for receiving data from said detector device.

4. The inspection system of claim 3, wherein said processor receives GPS data comprising the geographic location of said mast.

5. The inspection system of claim 3, wherein said scanned information is stored as data for later retrieval and analysis to determine one or more of level of external corrosion, level of internal corrosion, external weld cracks, internal weld cracks, external surface cracks, internal surface cracks, size and extent of holes, breaks, blemishes, defects, loss of surface finish, straightness and verticality of pole structure, extent of graffiti, bullet holes, missing parts, broken parts, geographic location, or elevation.

6. The inspection system of claim 3, wherein said scanned information is stored as data, which stored data post analyzed by human observation and interpretation to determine one or more of whether all components pass and are in good working order; whether any component fails and requires one or more of specific non-destructive testing or remedial action to repair said component; whether any component has an anomaly that requires further monitoring during subsequent inspections to determine the progression of the failure and to eventually predict future failure mode or timing.

7. The inspection system of claim 3, wherein said scanned information is stored as data, which stored data is used to schedule one or more of future inspections or maintenance tasks.

8. The inspection system of claim 3, wherein said scanned information is stored as data, which stored data is used to correlate failure modes.

9. The inspection system of claim 3, wherein said scanned information is stored as data, which stored data is used to create a history of structural behavior leading to eventual failure.

10. The inspection system of claim 1, wherein said detector device senses one or more of mast crack or mast flaw data.

11. The inspection system of claim 1, wherein processor analyzes said crack or flaw data by:

(i) receiving data that represents an actual width of a base portion of the mast;

(ii) receiving data that represents the distance between the base portion of the mast to a crack or flaw located in the mast;

(iii) receiving the actual width of the mast at a location of the crack or flaw;

(iv) receiving inputted location points that represent crack or flaw points and receiving inputted width points that represent width points; and (v) calculating the actual dimensions of the crack or flaw based on the relationship between the inputted crack or flaw points in (iv) and the inputted width points and the actual pole width of the subject crack or flaw as provided (iii).

12. The inspection system of claim 1, wherein said detector device is adapted to perform one or more of: detecting, inspecting, monitoring, positioning, or marking.

13. The inspection system of claim 1, wherein said mounting support assembly at least partially circumferentially surrounds said mast.

14. The inspection system of claim 1, wherein said mounting support assembly is at least partially disposed inside of said mast.

15. The inspection system of claim 1, wherein said mounting support assembly is at least partially disposed adjacent to said mast.

16. The inspection system of claim 1, wherein said mounting support assembly comprises a partial band member.

17. The inspection system of claim 16, wherein said partial band segment forms an arc shape.

18. The inspection system of claim 16, wherein said band member is adapted to have an adjustable diameter.

19. The inspection system of claim 1, wherein said mounting support assembly comprises a plurality of detachable segment members.

20. The inspection system of claim 1, wherein said detector device comprises a digital video camera and said mounting support assembly comprises a bracket assembly for removably affixing said digital video camera to said platform.

21. The inspection system of claim 1, wherein said mast is a high mast light pole and said platform is a luminaire ring.

22. The inspection system of claim 1, further comprising:

(e) a processor connected to said wireless communications transceiver for receiving data from said detector device.

23. A method for inspecting a generally upright mast having a platform movable along the vertical lengthwise extent of said mast, which comprises the steps of:

(i) installing an inspection system to said movable platform, said inspection system comprising:

(a) a mounting support assembly removably fixed to said platform;

(b) a detector device carried by said mounting support assembly; and (f) a processor connected to said wireless communications transceiver for receiving data from said detector device:

(ii) moving said platform along the vertical lengthwise extent of said mast;

(iii) collecting scanned information from said detector device correlative to one or more of mast cracks or mast flaws; and (iv) storing said scanned information as data for later retrieval and analysis to determine one or more of level of external corrosion, level of internal corrosion, external weld cracks, internal weld cracks, external surface cracks, internal surface cracks, size and extent of holes, breaks, blemishes, defects, loss of surface finish, straightness and verticality of pole structure, extent of graffiti, bullet holes, missing parts, broken parts, geographic location, or elevation.

24. The method of claim 23, wherein aid detector device is powered by a:

(c) power supply carried by one or more of said mounting support assembly or said detector device.

25. The inspection system of claim 24, wherein said detector device is adapted to perform one or more of: detecting, inspecting, monitoring, positioning, or marking.

26. The method of claim 23, wherein said inspection system further includes:

(d) a first wireless communication transceiver carried by one or more of said mounting support assembly or said detector device and connected to said detector device and connected to said detector device to receive data from said detector device; and (e) a remotely located, second wireless communications transceive/router in communication with said first wireless communication transceiver for receiving data from said detector device.

27. The method of claim 23, wherein said detector device senses one or more of mast crack or mast flaw data.

28. The method of claim 23, wherein processor analyzes said crack or flaw data by:
   (i) receiving data that represents an actual width of a base portion of the mast;
   (ii) receiving data that represents the distance between the base portion of the mast to a crack or flaw located in the mast;
   (iii) receiving the actual width of the mast at a location of the crack or flaw;
   (iv) receiving inputted location points that represent crack or flaw points and receiving inputted width points that represent width points; and
   (v) calculating the actual dimensions of the crack or flaw based on the relationship between the inputted crack or flaw points in (iv) and the inputted width points and the actual pole width of the subject crack or flaw as provided (iii).

29. The method of claim 23 wherein said processor receives GPS data comprising the geographic location of said mast.

30. The method of claim 23, wherein said scanned information is stored as data, which stored data post analyzed by human observation and interpretation to determine one or more of whether all components pass and are in good working order; whether any component fails and requires one or more of specific non-destructive testing or remedial action to repair said component; whether any component has an anomaly that requires further monitoring during subsequent inspections to determine the progression of the failure and to eventually predict future failure mode or timing.

31. The method of claim 23, wherein said scanned information is stored as data, which stored data is used to schedule one or more of future inspections or maintenance tasks.

32. The method of claim 23, wherein said scanned information is stored as data, which stored data is used to correlate failure modes.

33. The method of claim 23, wherein said scanned information is stored as data, which stored data is used to create a history of structural behavior leading to eventual failure.

34. An inspection system for removably mounting to a luminaire ring movable in relation to a generally upright high mast light pole for inspection of said mast, which comprises:
   (a) a mounting support assembly removably fixable to said luminaire ring;
   (b) a detector device carried by said mounting support assembly for scanning said mast and collecting mast scanned information;
   (c) a power supply carried by one or more of said mounting support assembly or said detector device and connected to said detector device; and
   (d) a communications device carried by one or more of said mounting support assembly or said detector device and connected to said detector device for receiving and relaying said collected high mast light pole scanned information.

35. The inspection system of claim 34, wherein said detector device is adapted to perform one or more of: detecting, inspecting, monitoring, positioning, or marking.

36. A method for inspecting a generally upright mast having a platform movable along the vertical lengthwise extent of said mast, which comprises the steps of:
   (i) installing an inspection system to said movable platform, said inspection system comprising:
      (a) a mounting support assembly removably fixed to said platform;
      (b) a detector device carried by said mounting support assembly; and
      (c) a processor connected to said wireless communications transceiver for receiving data from said detector device and for receiving GPS data comprising the geographic location of said mast;
   (ii) moving said platform along the vertical lengthwise extent of said mast; and
   (iii) collecting data from said detector device correlative to one or more of mast cracks or mast flaws.

37. The method of claim 36, wherein said scanned information is stored as data, which stored data post analyzed by human observation and interpretation to determine one or more of whether all components pass and are in good working order; whether any component fails and requires one or more of specific non-destructive testing or remedial action to repair said component; whether any component has an anomaly that requires further monitoring during subsequent inspections to determine the progression of the failure and to eventually predict future failure mode or timing.

\* \* \* \* \*